United States Patent [19]

Coffey et al.

[11] 4,098,130
[45] Jul. 4, 1978

[54] ENERGY REFLECTION FLAW DETECTION SYSTEM

[75] Inventors: William N. Coffey, Ballston Lake; George Jernakoff, Loudonville, both of N.Y.; John R. Zurbrick, Cincinnati, Ohio

[73] Assignee: General Electric Company, Schenectady, N.Y.

[21] Appl. No.: 776,589

[22] Filed: Mar. 11, 1977

[51] Int. Cl.² ............................................. G01N 29/04
[52] U.S. Cl. .......................................... 73/614; 73/602
[58] Field of Search ................... 73/67.7, 67.8 R, 67.9, 73/614, 602

[56] References Cited

U.S. PATENT DOCUMENTS

| | | | |
|---|---|---|---|
| 3,823,603 | 7/1974 | Couture | 73/67.9 |
| 3,972,228 | 8/1976 | Mansson | 73/67.7 |
| 3,986,389 | 10/1976 | Mesina | 73/67.9 |

*Primary Examiner*—Charles A. Ruehl
*Attorney, Agent, or Firm*—Geoffrey H. Krauss; Joseph T. Cohen; Marvin Snyder

[57] ABSTRACT

An energy reflection flaw detection system utilizes a programmable system synchronization means having high stability and resolution, to facilitate the detection of flaws within an object to be analyzed even in the presence of relatively large amplitude reflections from front and back surfaces of the object. A surface encounter attenuator is actuated by the system synchronizer to highly attenuate the front and back surface echoes and allow flaws closely adjacent to the surfaces to be resolved by the broadband apparatus. Novel means for adjusting the system gain to compensate for divergence of the interrogating energy beam with time and distance is also utilized in this novel apparatus.

14 Claims, 18 Drawing Figures

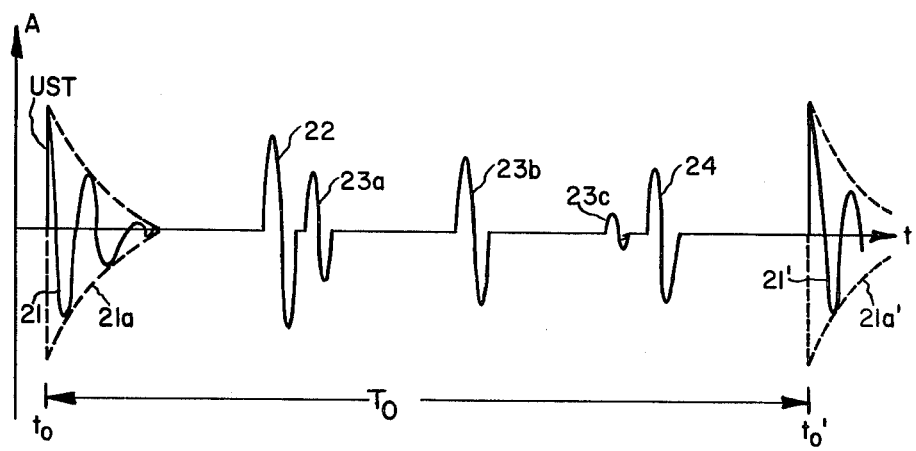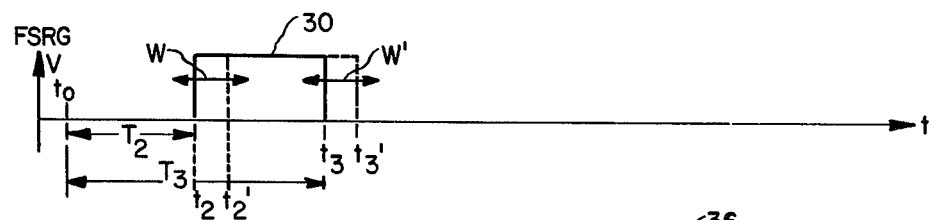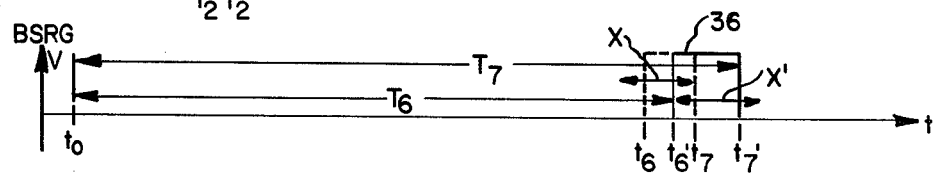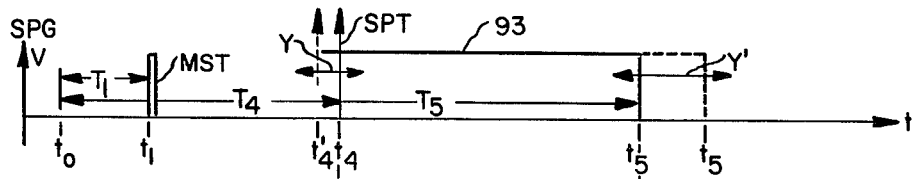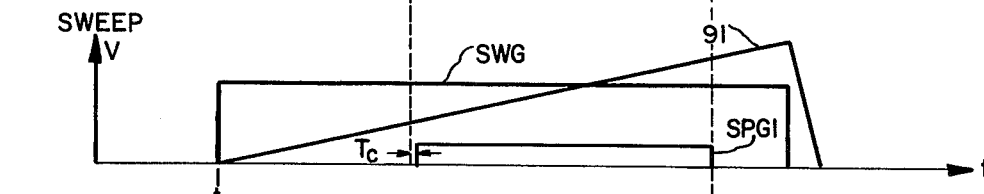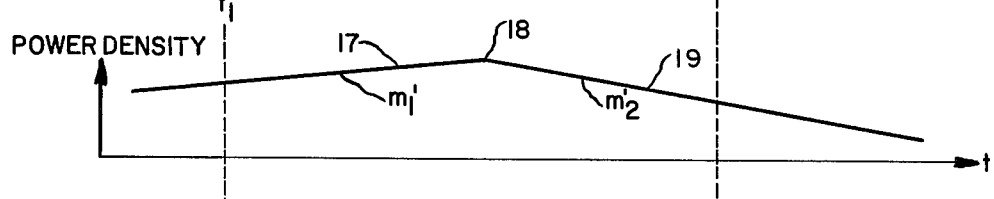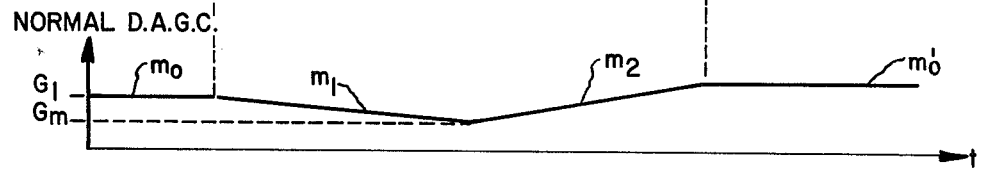

ENERGY REFLECTION FLAW DETECTION SYSTEM

BACKGROUND OF THE INVENTION

The present invention relates to non-destructive testing apparatus and, more particularly, to a novel energy reflection flaw detection system having high resolution and stability to facilitate removal or controlled attenuation of undesirable echoes from surfaces of the object of be analyzed and facilitating analysis of flaws closely adjacent to those surfaces, as well as throughout the volume of the object-under-test.

Known energy reflection flaw detection systems, such as conventional immersion ultrasonic flaw detectors, generally require improvement in timing accuracy, resolution and stability to provide the maximum meaningful data obtainable. In particular, flaws located near the surfaces of an object-under-test are often undiscernable, due to the reflection of energy from edges and surfaces of the object returning from the object at substantially the same time as the reflections from the flaw to be investigated, which flaw reflection is generally of lesser amplitude than the surface and/or edge reflection. Means for removing the surface reflections in highly stable and consistent fashion are therefore desirable. Similarly, a problem exists in that the beam of energy interrogating the object-under-test is often focussed at a point in the object, whereby the beam power density increases as the focal point in approached and then decreases thereafter, generating varying reflection amplitudes for equal magnitude flaws at different positions within the object, which (when combined with varying amplitude from a single flaw due to the non-uniformness thereof) often result in the largest flaws being ignored by the detection system in favor of relatively smaller flaws having a boundary surface disposed in such manner as to reflect somewhat greater energy in a greater power density portion of the beam. Therefore, means for offsetting the varying power density of the beam and means responsive to small portions of a reflected signal are desirable to alleviate this problem.

BRIEF SUMMARY OF THE INVENTION

In accordance with the invention, an energy reflection flaw detection system having means for generating a pulsed beam of energy toward and through an object to be analyzed, and means for receiving energy reflections therefrom and converting the same into electrical signals, includes a highly stable system synchronization means having high resolution for generating all system timing signals; a surface encounter attenuator means enabled by the system sychronizer means to variably attenuate the relatively large front and back surface reflection signals while substantially allowing the reflection signals from flaws within the object-under-test to pass with relatively little attenuation; a broadband programmable attenuator means; amplification means having gain variably dependent upon the time at which a signal is received after the pulse is generated to offset the effects of changes in beam power density; means for processing the signal to determine the magnitude of the flaw signal; and means for performing an alarm function if the flaw magnitude is greater than a predetermined set of maximum flaw magnitudes.

In one preferred embodiment, a signal processor means is preceded by a full-wave rectifier means, whereby both polarity portions of a reflection signal are recovered to assure that the peak reflection magnitude is available before processing.

The system synchronizer is adapted for programming both manually via a keyboard means and automatically via a set of external data and control lines interfacing with external means, such as a computer and the like, whereby the high stability and resolution of the cycle time between energy pulses and the timing of all system signals after the commencement of each cycle are advantageously utilized to acquire the maximum information available from each interrogation of the object to be analyzed.

Accordingly, it is one object of the present invention to provide a novel energy reflection flaw detection system capable of analyzing flaw reflections closely adjacent to potentially interfering surface reflections.

It is another object of the present invention to provide a novel energy reflection flaw detection system having means for presenting both polarity portions of a reflected signal for processing.

It is yet another object of the present invention to provide a system having a system timing sychronizer capable of providing all system times and cycle times (pulse repetition rate) with high stability and resolution.

It is still another object of the present invention to provide a novel system having means for offsetting the effect of varying energy beam power density with time and distance to the object to be analyzed.

These and other objects of the present invention will become more apparent upon consideration of the following detailed description and the associated drawings.

BRIEF DESCRIPTION OF THE DRAWINGS

FIG. 2 is a graph of system transponder signals, with respect to time, typically encountered in the embodiment of FIG. 1;

FIGS. 3a-3d are system signal waveforms coordinated in the time domain with the graph of FIG. 2;

FIGS. 4a and 4b are graphs, coordinated with the graphs of FIGS. 2 and 3a-3d, illustrating the change in power density with time (and therefore distance) and the Distance Automatic Gain Control function;

FIG. 5c is a graph illustrating the time relationship between control signals emanating from the circuitry of FIG. 5a;

DETAILED DESCRIPTION OF THE INVENTION

Figure 1:
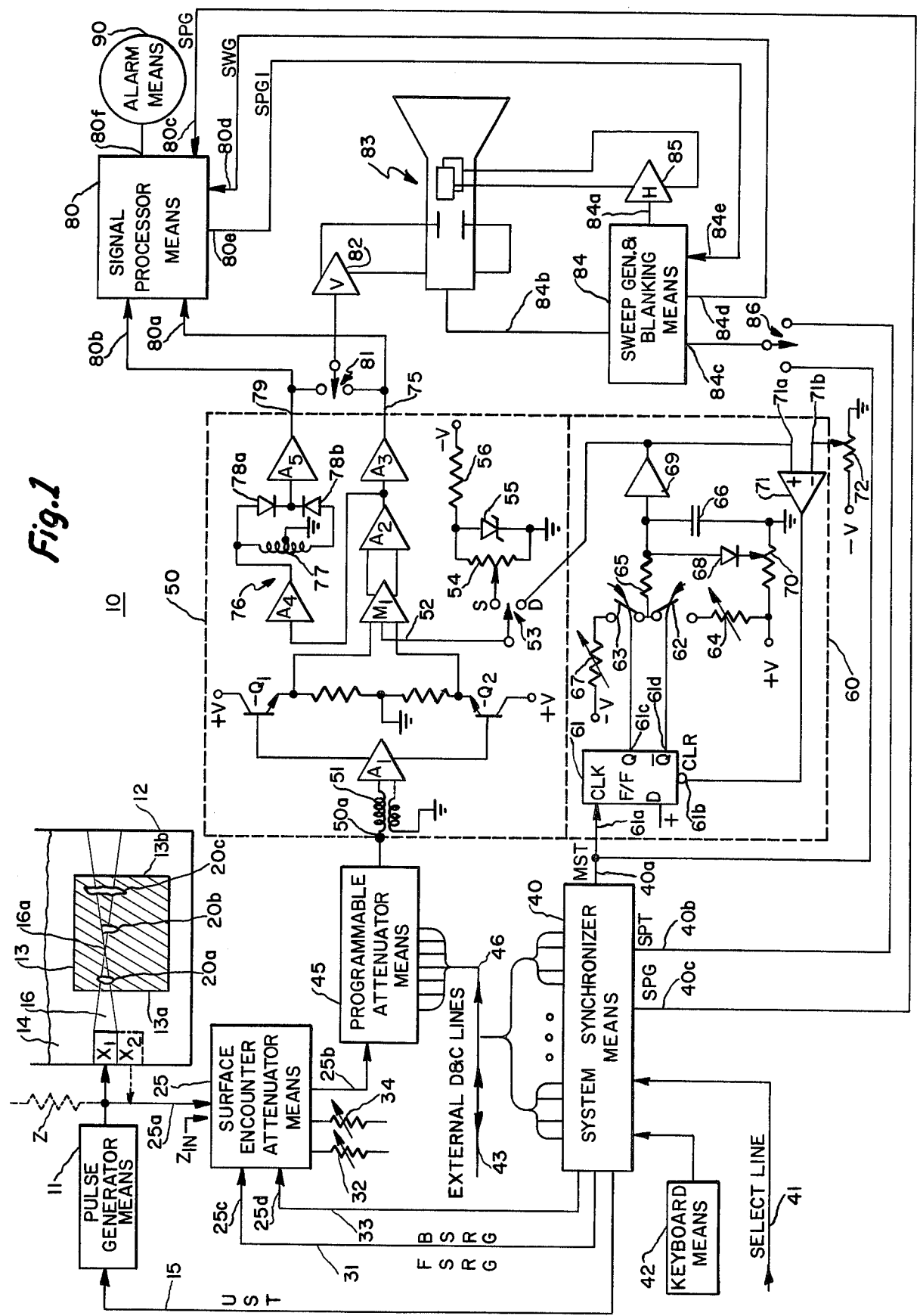
FIG. 1 is a partially-schematic block diagram of one embodiment of an energy reflection flaw detection system, utilizing immersion ultrasonic techniques, in accordance with the principles of the present invention.

Referring initially to FIGS. 1, 2, 3a-3d, 4a and 4b, one preferred embodiment of an energy reflection flaw detection system 10, especially configured for immersion ultrasonic flaw detection usage, comprises a pulse generator means 11 driving at least one ultrasonic transducer $X_1$ located within a tank 12 containing a member 13 which is to be examined for internal flaws. Member 13 is immersed within a quantity of liquid 14, filling tank 12 to provide a uniform transmission medium between the transducers and object 13. Responsive to receipt of an ultrasonic trigger pulse (UST) on line 15, pulse generator means 11 applies a pulse of electrical energy to a transmitting transducer (illustratively, single transducer $X_1$) to emit a beam 16 of energy towards the nearest, or front, surface 13a of the object to be studied. Beam 16 travels through object 13, emerging from the furthest, or back, surface 13b thereof. Beam 16 is generally focussed at a point 16a lying within the confines of object 13, whereby the beam power density (FIG. 4a) is not uniform, i.e. the power density of pulsed beam 16 (with the pulse being located at increasing distances from the emitting transducer for increasing time after the UST pulse) is an increasing power density as focal point 16a is approached (increasing power density portion 17 of FIG. 4a), reaching a peak at focal point 16a (peak 18 of the power density curve of FIG. 4a) and thence having a monotonically decreasing power density (portion 19 of FIG. 4a) from focal point 16a to back surface 13b.

In the preferred embodiment, the system is utilized to detect flaws occurring as voids 20 within object 13. The flaws 20a–20c may be of varying sizes in a plane transverse to the direction of beam propagation and of varying depths in the direction of beam propagation. A portion of the energy of beam 16 is reflected at each of the object front surface 13a; the edges and within the voids of each of flaws 20a–20c, and the object back surface 13b. This reflected energy is received at the transducer at a time, after transmission of the beam pulse (responsive to receipt of the UST signal), proportional to the round trip distance between the transducer and the reflecting surface or volume. It should be understood that one or more transducers may be simultaneously pulsed to produce beam 16 having desired spatial characteristics, and that the transmitting transducer(s) may be utilized for reception of the reflected energy, or that one or more additional transducers $X_2$ may be utilized only for receiving the reflected energy while the one or more pulse transducers $X_1$ serve only as transmitting means. The use of separate transmission and reception transducers may require appropriate means therebetween to protect the receiving transducers during the formation of the transmitted pulse.

The transmitting transducer $X_1$ is in electrical parallel connection with some impedance Z (which may be the impedance of the receiver transducer protection means or the input impedance $Z_{in}$ of the receiver, also coupled in electrical parallel connection across the transducers), which impedance Z serves to damp the envelope 21a (FIG. 2) of the ultrasonic pulse 21, whereby after several cycles (typically 1–3 cycles) of ultrasonic oscillation (typically at frequencies between 2.5 MHz. and 20 MHz.), the transmitted ultrasonic pulse has been damped to exponentially decay to approach a substantially zero amplitude signal. It is preferable that the impedance in parallel with the transmitting transducer is substantially resistive both at the fundamental frequency of the transducer and at the lower harmonics thereof, e.g. to about 10 times the fundamental frequency, to damp the various frequency components of the relatively wide-band pulse signal.

In the time domain (FIG. 2), the UST pulse triggers the high energy impulse, or so-called "big bang", 21 prior to its rapid exponentially decay towards zero amplitude. The beam energy pulse propagates through liquid 14 and a front edge encounter echo signal 22 arrives at the receiving transducer at a finite time, between a minimum time interval $T_2$ and a maximum time interval $T_3$, after the start of the "big bang" at time $t_0$. The remaining beam energy propagates through object 13 until a portion thereof is reflected by first flaw 20a as a first flaw signal 23a. At some later time, other portions of the beam energy are reflected back from second flaw 20b, third flaw 20c and the back surface 13b, respectively, as second and third flaw signals 23b and 23c, respectively, and as a back surface encounter echo signal 24. Advantageously, the ultrasonic pulse repetition period $T_0$, between the UST signals triggering pulse 21 and the next succeeding pulse 21', at time $t_0'$, is established to be greater than the round-trip time for the last signal of interest, e.g. the back surface encounter echo 24.

The entire echo signal is presented to the input port 25a (FIG. 1) of a surface encounter attenuator (SEA) means 25, having a substantially constant input impedance $Z_{in}$ over the desired wide range of frequencies including the fundamental and lower harmonics of the ultrasonic pulse frequency. SEA means 25 normally has a relatively low value of attenuation for signals exiting from its output port 25b, relative to the amplitude of signals entering input port 25a. In order to allow flaws adjacent to the object front surface 13a to be detected, without their echo signal, e.g. signal 23a, being lost in the substantially greater amplitude front surface echo signal 22, the attenuation between ports 25a and 25b is increased during the time period commencing at a time $t_2$ prior to the earliest echo from front surface 13a and ending at a time $t_3$ immediately after the last of the front surface reflected energy is received at attenuator input 25a. The front surface echo is suppressed responsive to receipt of a front surface reflection gate (FSRG) signal 30 (FIG. 3a), presented to SEA means control input 25c on an FSRG line 31. The attenuation during the FSRG pulse 30 is variable by means of a first control 32, forming part of SEA means 25, while the magnitude of normal attenuation is variable established by means of an additional control as hereinafter explained. Similarly, the measurement of a flaw reflection signal, e.g. signal 23c, at a position adjacent the rear surface 13b of the object may require an increase in the attenuation of SEA means 25 during the time interval when the back surface reflection signal 24 is present. SEA means 25 is enabled to its high attenuation condition, during the back surface reflection, by means of a back surface reflection gate (BSRG) signal 36 (FIG. 2b) arriving at second control input 25d via a control line 33. The magnitude of attenuation enabled responsive to receipt of BSRG is independently adjustable by means of a second control 34. It should be understood that the FSRG signal 30 must have both a variable duration ($T_3$-$T_2$) and a variable delay $T_2$ after the UST time $t_0$, e.g. FSRG start time $t_2$ and stop time $t_3$ must be accurately and variable controlled relative to time $t_0$, whereby the FSRG start time may be adjusted in the directions of arrows W, to occur between some earliest time $t_2$ and some latest time $t_2'$, and the FSRG stop time can be adjusted in the directions of arrows W', to occur between some earliest time $t_3$ and some latest time $t_3'$, as required for suppression of the front surface echo signal 22. Similarly, the start and stop time intervals $T_6$ and $T_7$, respectively, of the BSRG time interval 36 must also be precisely controlled whereby the start of the BSRG signal may be easily adjusted in the directions of arrows X to occur between some earliest time $t_6$ and some latest time $t_6'$, while allowing the later edge of the BSRG signal to be adjusted in the direction of arrows X' to occur between earliest and latest times $t_7$ or $t_7'$.

It will be seen that establishment of the various start and stop times for each of the FSRG and BSRG signals must be each independently and stably synchronized to the main pulse start time $t_0$ to assure system stability and resolution for detecting flaws closely adjacent one of the front and back surfaces. The highly accurate and stable FSRG and BSRG signals are provided by a system synchronizer means 40, which also provides the UST signal on line 15 to pulse generator means 11, in a manner more fully described hereinbelow. It is emphasized at this point that system synchronizer means 40 is programmable, and establishes the values of all time delays, including delays $T_0$, $T_2$, $T_3$, $T_6$ and $T_7$ hereinabove discussed, as selected (via select line 41) either from an associated manually-activated data entry keyboard means 41 and/or signals on a set of external data and control lines 43 from an external controlling means, such as a computer and the like (not shown). The ability to be commanded by an external computer is particularly advantageous, in that the values initially established for various function times, such as the commencement and cessation of FSRG at $t_2'$ and $t_3'$, respectively, may be incorrect, whereby the computer may rapidly evaluate the signals received during a signal echo period $T_0$ and re-command the system to establish new time values, e.g. commencement and cessation times $t_2$ and $t_3$, respectively, which accomplish the desired purpose, e.g. attenuating the front surface echo without attenuating the echo signal 23a from the first flaw 20a immediately beneath the front surface.

It should be understood that surface encounter attenuation means 25 may be removed from the system, if desired, by coupling input 25a directly to output 25b, as by means of a relay or the like (not shown for purposes of simplicity). Similarly, the surface encounter attenuator means may be effectively removed by programming the FSRG and BSRG time intervals to approach zero, i.e. cessation times $t_3$ or $t_7$ to be immediately after the respective gate commencement times $t_2$ or $t_6$, respectively.

The signal from SEA means output port 25b is attenuated by a programmable (broad bandwidth) attenuator means 45 to establish a desired signal amplitude at the input 50a of a front end amplifier means 50. Attenuator means 45 is advantageously programmable in binary fashion by means of a set of binary coded electronic signals formed on a group of control lines 46. The binary data on control lines 46 may be established by a manually settable control, such as on a front panel of the system, or may be entered under programmable control of an external computer means. Known multiplex selection techniques may be utilized to determine which of the two sets of binary control signals are presented to attenuator means 45.

Front end amplifier means 50 constitutes a wideband amplifier normally having a fixed high gain. The wide bandwidth characteristics of amplifier 50 allow a wide frequency range of ultrasonic detectors to be utilized without requiring adjustments to tune the passband of the amplifier to the frequency of the transducer, as is common with many conventional energy reflection flaw detection systems. A bifilar transformer means 51 not only provides input impedance matching between attenuator means 45 and amplifier 50, but also provides a balanced signal to a first differential amplifier $A_1$. The differential outputs of amplifier $A_1$ are each buffered by an emitter follower, comprising one of transistors $Q_1$ and $Q_2$, and are applied to the differential inputs of a balanced modulator means $M_1$. The gain of balanced modulator $M_1$ is variable responsive to the voltage at a control input 52 thereof. Control input 52 is coupled, via a switch 53, to a standard (time-invariant) gain adjust voltage S (established by the variable setting of the arm of a potentiometer 54 having a constant voltage established thereacross by means of a Zener diode 55 in series with a dropping resistor 56, coupled across a negative voltage source ($-V$)). The remaining contact of switch means 53 provides a time-variable voltage D utilized to normalize the effects of varying power density (as previously mentioned hereinabove and shown in FIG. 4a). The normalized distance-automatic gain control (DAGC) amplification (FIG. 4b) is maintained at some value $G_1$ during the "big bang" and until some time $t_1$ thereafter, before being caused to decrease with a slope $m_1$ approximately equal in magnitude to the magnitude of the slope $m_1'$ of the increasing power density curve portion 17 (FIG. 4). The minimum gain $G_m$ of the balanced modulator-amplifier $M_1$ is reached at essentially the same time as the peak 18 of the beam power density; thereafter, the gain of amplifier stage $M_1$ is increased with slope $m_2$, inversely proportional to the slope $m_2'$ of the decreasing power density curve portion 19. In this manner, the effect of nonuniform power density (with time and distance) upon the amplitude of flaw echoes 23 is minimized. It should be understood that, as flaw information is only generated within sample 13, DAGC control is not absolutely necessary prior to at least the front surface echo nor after the back surface echo, as indicated by the relatively flat gain portions $m_0$ and $m_0'$, respectively, prior to and after the front surface and back surface echo times respectively.

The DAGC means 60 (FIG. 1), providing voltage D to switch means 53 to achieve the time-variable gain in controlled amplifier $M_1$, includes a flip-flop (F/F) means 61, preferably of the edge-triggered D type. The D input is coupled to a positive potential (binary one) while the clock input 61a is coupled to a monitor scope trigger (MST) output of system synchronizer means 40. Prior to receipt of a binary one MST signal, the voltage at a clear (CLR) input 61b of F/F means 61 is a binary zero, whereby the Q and $\overline{Q}$ outputs 61c and 61d, respectively, are respectively set to binary zero and binary one states. The binary one state at the the $\overline{Q}$ output closes a first switch means 62 to apply a positive voltage ($+V$) through a variable series resistance 64 and a fixed series resistance 65 to a timing capacitor 66. A second switch means 63, receiving the binary zero voltage at the Q output, is in its open position, whereby a variable resistance 67 is not coupled to resistance 65. The anode of a diode 68 is coupled to the junction between resistance 65 and capacitance 66, as is the input of a buffer amplifier 69. The cathode of diode 68 is coupled to the adjustable arm of a potentiometer 70, having its end contacts coupled between the positive voltage ($+V$) and potential ground. With switch means 62 closed, capacitance 66 charges through variable resistor 64 and fixed resistor 65 to some positive voltage. Diode 68 and potentiometer 70 establish a maximum voltage at the input to buffer amplifier 69, which voltage cannot be exceeded and which establishes the maximum value of buffer output voltage D. Buffer output voltage D is also coupled to the positive input 71a of a voltage comparator means 71, having its negative input 71b coupled to the variable arm of a potentiometer 72, in parallel connection between a negative potential ($-V$) and ground potential. The voltage at negative input 71b is established such that when capacitor 66 is charged to its maximum positive voltage, the comparator output voltage is sufficiently positive to prevent activation of the CLR input 61b of F/F 61.

The rising edge, at time $t_1$, of the MST signal at output 40a appears at the clock (CLK) input 61a of the flip-flop and, as the data D input is always maintained at a binary one, clocks the binary one level through to the Q output 61c, while switching the $\overline{Q}$ output 61d to the binary zero level. Responsive thereto, switch means 62 opens and switch means 63 closes, whereby capacitor 66 begins to charge toward the negative potential ($-V$) through fixed resistor 65 and variable resistor 67. Thus, the DAGC voltage D begins to ramp in a negative voltage direction, at the output of buffer amplifier 69, causing a reduction in the gain of the modulator-amplifier $M_1$ stage. The slope $m_1$ of the gain reduction voltage is established by adjustment of potentiometer 67. When the buffer amplifier output voltage D reaches a negative voltage equal to the voltage established by the setting of potentiometer 72, the positive input voltage no longer exceeds the negative input voltage and the comparator output switches, providing a binary zero level at the CLR input of flip-flop 61. The Q output returns to the binary zero level, opening switch means 63, while the $\overline{Q}$ output returns to the binary one level, closing switch means 62, to cause capacitor 66 to charge towards the positive potential ($+V$) through fixed resistor 65 and variable resistor 64 with a gain slope $m_2$ established by the setting of potentiometer 64. The time at which the gain switches, corresponding to peak 18 in the power density curve, is established by potentiometer 72.

After gain correction for power density, the differential signals at the outputs of modulator-amplifier $M_1$ are amplified by an additional amplifier means $A_2$ and the amplified waveform is buffered by an output buffer means $A_3$ before its appearance on R.F. line 75. The amplified R.F. waveform at the output of amplifier $A_2$ is further amplified by another amplifier means $A_4$ and is applied to a full-wave rectifier means 76 comprising a balanced transformer means 77 and a pair of diodes 78a and 78b, each having a like electrode coupled to an opposite end of transformer means 77 and their remaining like electrodes coupled together to the input of another output buffer means $A_5$. The full-wave rectified video appears on another output line 79, and is particularly advantageous for use where the reflected signal may have one or more peaks of one polarity which are greater in amplitude than the largest peak of the other polarity. Conventional systems utilizing a half-wave rectifier means process peaks of only one polarity and information concerning peaks of the remaining polarity (which may indicate a larger magnitude flaw) is lost; our use of a full-wave rectifier means overcomes this problem.

Both the amplified R.F. (line 75) and the full-wave rectified video (line 79) are applied to respective inputs 80a and 80b of a signal processor means 80. A switch means 81 is utilized to select one of the R.F. output and full-wave rectified video output lines 75 and 79, respectively, for coupling to the amplitude input of a display means, such as the vertical amplifier 82 of a CRT display 83 or the like. A sweep generator and blanking means 84 provides a sweep voltage at a first output 84a for use by the display, e.g. the horizontal amplifier means 85 associated with the illustrated CRT display means 83. Sweep generator and blanking means 84 also provides a blanking signal at another output 84b for variably attenuating or increasing the brightness of the display trace.

Sweep generator means 84 is triggered by a signal received at a first input 84c, which may advantageously be selected to be the MST signal, occuring at time $t_1$, or a signal processing trigger (SPT) signal (to be described more fully hereinbelow) originating at output 40b of the system synchronizer means 40, with trigger signal selection occurring via a switch means 86.

To assure proper signal processing and display, a signal processing gate (SPG) signal is made available at an input 80c of signal processor means from an output 40c of system synchronizer means 40; a sweep width gate (SWG) signal from output 84d of sweep generator means 84 is made available at a signal processor input 80d; and an internal signal processing gate (SPGI) signal from a signal processing means output 80e is made available at sweep generator means input 84e. An alarm output 80f, of signal processor means 80, is utilized to activate one or more alarm means 90, including visible, audible or electronic control means, when a previously selected set of flaw size, number, etc. criteria are exceed in the object 13 under evaluation.

Referring now to FIGS. 3c and 3d, the effect of the SWG, SPG, SPT and SPGI signal will be described. As previously described hereinabove, at time $t_1$, accurately established after the commencement of a "big-band" pulse at $t_o$, the MST signal appears at system synchronizer means output 40a. In addition to controlling the commencement of the DAGC function, the MST signal at sweep generator means input 84c causes the commencement of a linear ramp sweep voltage 91, appearing at output 84a. The appearance of the increasing ramp portion of the sweep voltage generates a rectangular SWG waveform at sweep generator means output 84e, to gate signal processor means 80 from a dormant to an active state during the duration of the SWG signal.

At a time $t_4$, having a time interval $T_4$ independently established after the cycle initiation time $t_0$, and variable between time limits, e.g., $t_4$ or $t_4'$, as indicated by arrows Y, the SPT signal is generated by system synchronizer means 40 to signify that the first surface echo 22 has ended and to cause commencement of the signal processing gate (SPG) signal 93. The SPG signal has a time duration of $(T_5-T_4)$, where $T_5$ is the time interval between UST (at $t_0$) and the cessation time $t_5$ of the SPG signal. The SPG cessation time is also established in highly stable manner, and is adjustable between some minimum and maximum time, e.g., $t_5$ or $t_5'$, as indicated by arrows Y', to allow signal processing to cease immediately prior to the back surface echo 24, if desired. The SPT signal is also made available at system synchronizer means output 40b triggering sweep generator means 84, if selected by switch means 86, to modify the time at which sweep 91 starts and display only events occurring between the front and back surface echoes. Signal processor means 80 generates, as hereinbelow more fully explained, and transmits the SPGI signal to sweep generator means 84 for intensification of the display trace during SPG signal processing, but after reset (which occurs substantially immediately after commencement of SPG) of the processing circuits, as explained hereinbelow.

Figure 5C:
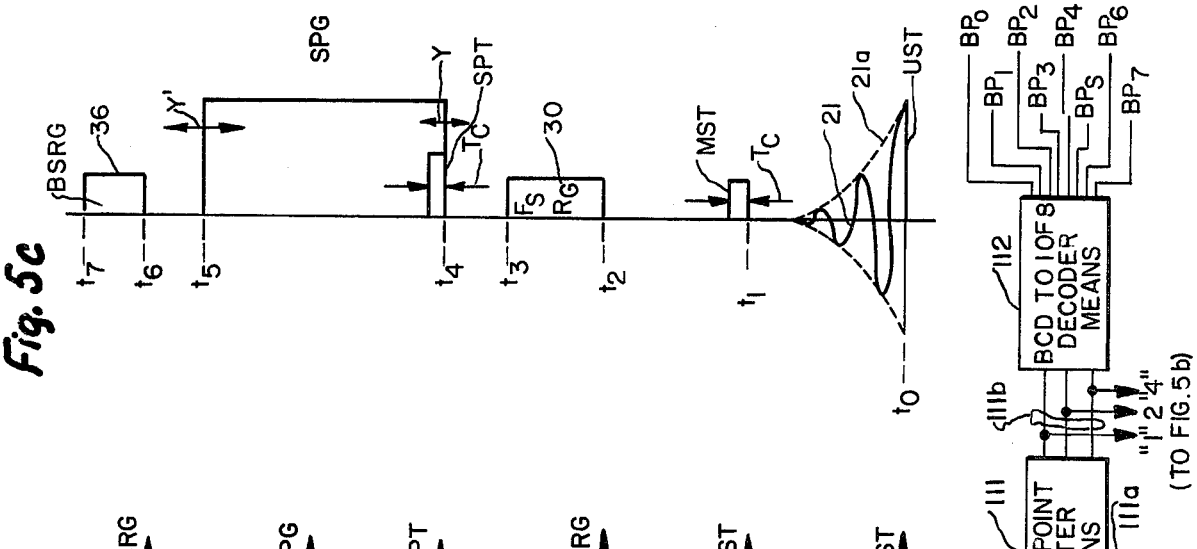
Figure 5A:
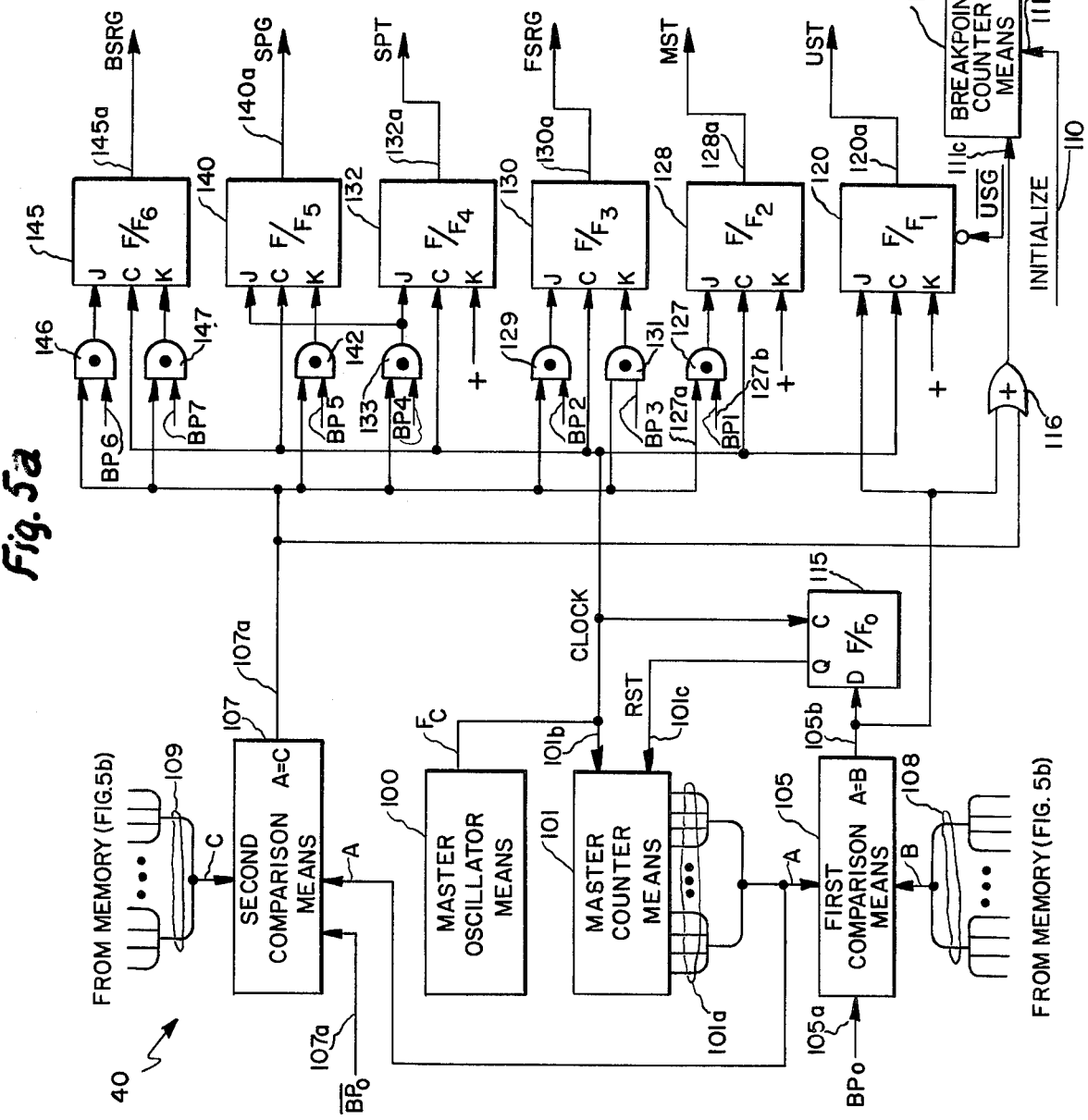
FIGS. 5a and 5b are a schematic block diagram of the system synchronizer means utilized in the embodiment of FIG. 1.
Figure 5B:
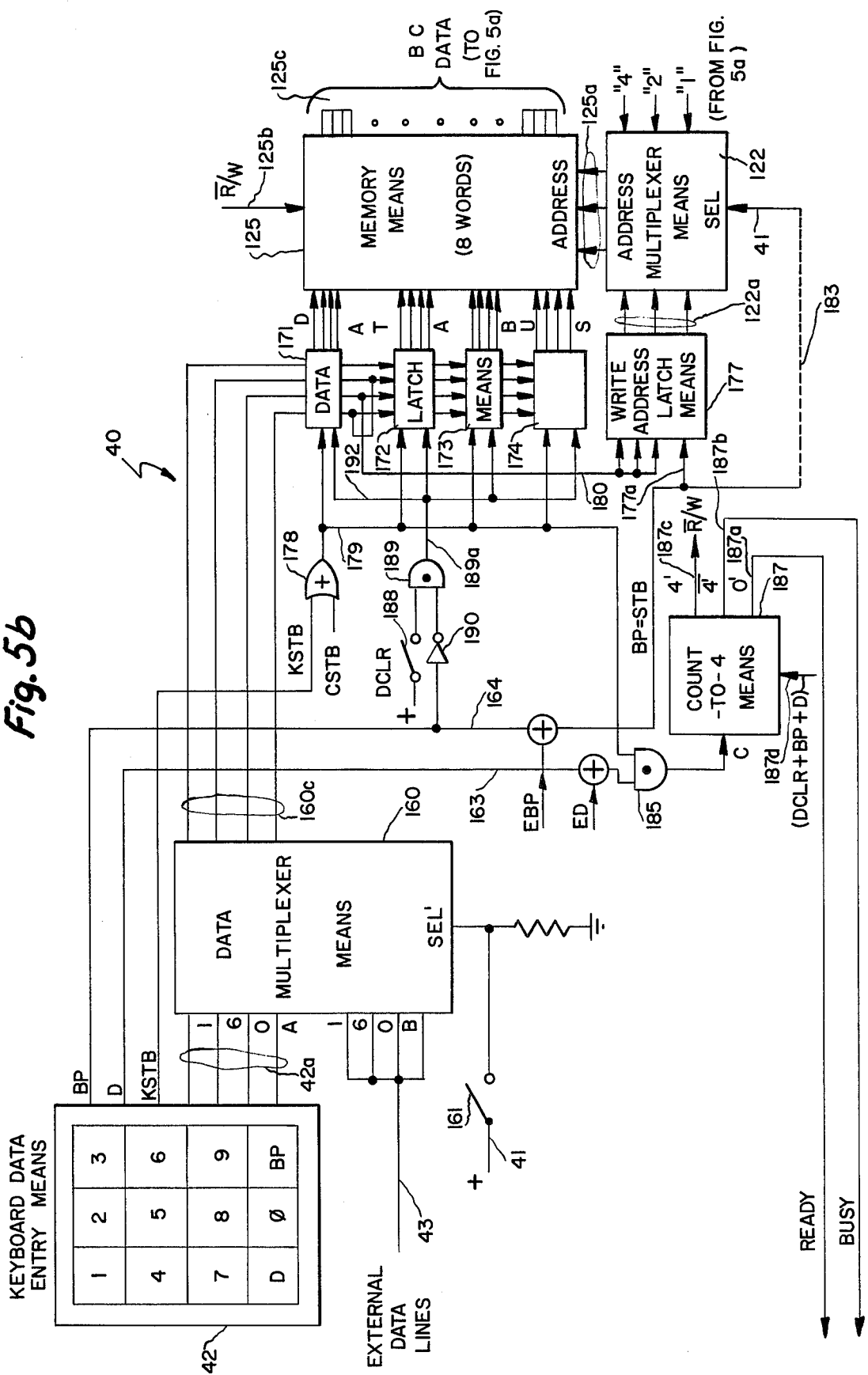

Referring now to FIGS. 5a–5c, one preferred embodiment of a system synchronizer means 40 is shown which is capable of providing the stable and highly resolvable variable commencement and cessation times for the MST, FSRG, SPG, SPT, BSRG signals and the repetition interval between UST trigger pulses, i.e., synthesization of all time intervals $T_0$ through $T_7$ in highly stable manner. The synchronizer means comprises a master oscillator means 100 having an output frequency $F_c$, selected as the inverse of the clock pulse interval $T_c$ required for resolution. Thus, to resolve each pulse to the nearest 0.1 microsecond, master oscillator means 100, preferably being temperature compensated and crystal controlled, has an output frequency of 10 MHz. A master counter means 101 provides a set of output lines 101a upon which the counting state of means 101 is present responsive to the sequential counting of clock pulses appearing at a clock input 101b, after removal of a reset (RST) signal at a second input 101c. The count output 101a is coupled to the A word inputs of a first comparison means 105 and a second comparison means 107, respectively. A set of lines 108 carries a plurality of numerical signals comprising a B word to another input to first comparator means 105, while another set of lines 109 provides a third, or C, word to second comparison means 107. In our preferred embodiment, data words A, B and C are of binary-coded decimal (BCD) data, although it should be understood that other data counting-coding schemes (such as binary, octal, hexadecimal and the like) could be utilized if desired. Each input A, B and C has four BCD decades, although a greater or lesser count could be utilized, dependent upon the total range and resolution required.

The flaw detector system is activated by generating a pulse on an Initialize line 110 to a rest input 111a of an eight-sequential-state breakpoint counter means 111. Upon receipt of the Initialize pulse, the three binary coded outputs 111b, thereof, e.g., the "1", "2"and "4" binary lines, are initialized to each have a binary zero signal thereon. These signals are coupled to a BCD-to-one-of-eight decoder means 112, causing its breakpoint-zero (BP$_0$) output to be raised to a binary one level. The binary-one BP$_0$ signal appears at a first comparison means enable input 105a, to activate the first comparison means whereby an A"B output 105b thereof is energized only during the one clock-pulse interval when the first input A, from master counter means 101, is equal to the data at the B input. The binary-one state at output 105b appears at the D input of a D-type flip-flop (F/F$_0$) means 115, which also receives the clock signal from master oscillator means 100 at a clock C input. The presence of a clock pulse simultaneous with application of the binary-one signal at the D input causes the output Q of F/F$_0$ to switch to a binary-one state whereby a reset signal appears at the RST input 101c of master counter means 101 to reset the count outputs 101a thereof of zero. After reset, master counter means 101 commences counting and eventually reaches a count state equal to the number at input B of the first comparison means, to energize the equivalence output 105b for one clock pulse width. The equivalence signal resets the counter means to zero after each count time interval, establishing the time interval $T_0$ of each system cycle between successive UST signals.

The binary-one signal at equivalence output 105b is also coupled, via an OR gate 116, to the count input 111c of breakpoint counter means 111, whereby the count at output 111b advances to the next state, e.g., a binary code of 001 on output lines "4", "2" and "1". Decoder means 112 decodes this count to energize only its BP$_1$ output. The binary-one state at first comparison means output 105b is also coupled to the J input of a flip-flop (F/F$_1$) means 120, which also receives the clock pulse output of master oscillator means 100 at its clock input C. The presence of a binary-one at the J input, in addition to a clock signal at the C input, causes the output 120a of F/F$_1$ to be enabled at time $t_0$ to issue the UST signal triggering a "big bang" and initiating a cycle of the energy reflection flaw detection system. The K input of F/F$_1$ is coupled to a positive potential, whereby, upon receipt of the next subsequent clock pulse, output 120a and the UST signal are disabled. Thus, the UST signal is a one-clock-pulse wide signal having high stability (as insured by the high stability of master oscillator means 100) and the time interval $T_0$ between UST pulses is achieved within the resolution of the master oscillator frequency $F_c$.

The appearance of any breakpoint other than the zero-th breakpoint (BP$_O$) temporarily disables first comparator means 105 but enables second comparison means 107 at the $\overline{BP_O}$ input 107a thereof. The breakpoint counter means outputs 111b are transmitted via an address multiplex means 122 (FIG. 5b) to the address port of a memory means 125. The memory means stores a number of data words, equal in number to the number of independently-selectable times (or breakpoints) as required by the system. At the initiation of a system cycle, the binary 000 address is present at the address input of memory means 125 and, in conjunction with a binary zero signal on a read-write ($\overline{R/W}$) input 125b, causes the binary data pattern associated with BP$_O$ to appear at the data output 125c of the memory means to establish the B word and, hence, the cycle time. The first activation of breakpoint counter input 111c changes the binary data pattern at memory means address input 125a to the 001 pattern for BP$_1$, whereby (with a binary zero, or read, signal at input 125b) the BP$_1$ binary data is caused to appear at the C input of second comparison means 107 at a time when counter means output A indicates a count close to zero, but less than the count associated with the first breakpoint time $t_1$. Master counter means 101 is continuously incremented and eventually cause the data A lines to be enabled with a binary count data pattern equivalent to the data C data pattern, whereupon an A=C output 107b is energized only for that single clock cycle during which the two data patterns are bit-by-bit equivalent.

Activation of equivalence output 107a is coupled to a first input 127a of a two-input AND gate 127, receiving the binary-one BP$_1$ at its remaining input 127b from the BP$_1$ output of decoder means 112. The AND gate forms a binary-one signal at the J input of a flip-flop (F/F$_2$) means 128, to energize the output 128a thereof and form the MST signal at the time $t_1$, coincident with the appearance of a clock signal at the C input of F/F$_2$. The J input is returned to a binary-zero state before the next successive clock pulse, whereby the binary-one signal at the K input of F/F$_2$ returns output 128a to the de-energized state to provide the MST signal with a time interval $T_c$ of the clock pulse.

The activation of equivalence output 107a appears, via OR gate 116, at breakpoint counter means 111 to advance the counter at the binary data pattern 010 (decimal 2) to simultaneously energize only the $BP_2$ output of decoder means 112 and to re-address memory means 125 to cause the binary data pattern C at the output 125c thereof to represent the binary count associated with the next sequential system time, e.g., commencement of FSRG at $t_2$.

Master counter means 101 continues incrementing its A count output 101a. The count output eventually becomes bit-by-bit equivalent to the $BP_2$ data at the C input of second comparison means 107, whereupon equivalence output 107b is again energized and is then gated via another AND gate 129, having the binary-one $BP_2$ signal appearing at one of its inputs, to the J input of a flip-flop ($F/F_3$) means 130. Simultaneous energization of the J and clock C inputs of $F/F_3$ energize the output 130a thereof to commence generation of the FSRG signal at time $t_2$. The J input reverts to a binary-zero state by the next subsequent clock pulse, but the K input of $F/F_3$, being derived from an AND gate 131 having the now-deactivated equivalence output 107a coupled to an input thereof, is now a binary-zero signal, whereby $F/F_3$ output 130a remains in the activated condition.

Breakpoint counter means outputs 111b are advanced to a binary 011 pattern (decimal 3) and decoder means 112 energizes only its $BP_3$ output in response thereto. Memory means 125 receives the binary 011 address input to cause the binary data pattern associated with the third breakpoint (for the next required time $t_3$, or the time interval $T_3$ between the end of FSRG and the beginning of the system cycle at $t_O$). The $t_3$ data pattern appears at the C input to second comparator means 107 and, when master counter means 101 has reached the same count, the equivalence output 107a is again energized to activate the output of AND gate 131, whereby $F/F_3$ output 130a is de-energized, completing the FSRG time interval.

Similarly, the enablement of equivalence output 107a advances breakpoint counter means 111 to cause memory means 125 to present the data pattern for the next breakpoint ($BP_4$), while decoder means 112 energizes only the $BP_4$ output. Second comparison means 107 monitors the two data patterns and its equivalence output at the coincidence thereof, to energize the J input, via AND gate 133, of another flip-flop ($F/F_4$) means 132. The output 132a of $F/F_4$ means is energized for a single clock cycle, due to the constant binary-one signal at the K input thereof, to generate the signal-clock-cycle wide SPT signal at time $t_4$.

The binary-one signal at the J input of $F/F_4$ also appears at the J input of another flip-flop ($F/F_5$) means 140 to energize the output 140a thereof to commence the SPG signal. The SPG signal can be present for longer than a single clock pulse, as the K input of $F/F_5$ is not coupled to a constant binary-one signal. Breakpoint counter means 111 is advanced to cause memory means 125 to present the data C word associated with the next breakpoint ($BP_5$) and decoder means 112 energizes only its $BP_5$ output, coupled to one input of an AND gate 142. Upon master counter means 111 counting to the time required by the $BP_5$ data pattern at input C of second comparison means 107, equivalence output 107a is again enabled to cause AND gate 142 to energize the K input of $F/F_5$ and, during the presence of a clock pulse at the C input thereof, de-energizes output 140a of $F/F_5$ to stop the SPG signal at time $t_5$.

Next, counter means 111, decoder means 112 and memory means 125 are again activated by the $BP_5$ coincidence signal. The proper data for $BP_6$ is presented to the C input of means 107 and eventually enables the J input of a last flip-flop ($F/F_6$) means 145, via an AND gate 146, at time $t_6$. The $F/F_6$ output 145a is enabled to commence the BSRG signal. The counter, decoder and memory means are again updated to provide the data C word for the last breakpoint $BP_7$ and, at some time thereafter, A=C coincidence occurs to cause the K input of $F/F_6$ to energized via an AND gate 147, to de-energize the flip-flop output 145a and terminate the BSRG signal at the desired time $t_7$.

The enablement of equivalence output 107a associated with $BP_7$ also enables breakpoint counter means 111 to its next sequential state. Output lines 111b now carry the binary data patterns 000 (decimal 0) which appears at memory means address input 125a. The binary data now present at input B of first comparator means 105 is that data pattern corresponding to the total cycle time $T_O$ of the system. Decoder means 112 has activated its $BP_O$ output, disabling second comparison means 107 and enabling first comparison means 105. When master counter means 101 outputs the count equal to the $BP_O$ data pattern on lines 108 of the memory means, the first comparison means output 105b is energized to reset the master counter means to zero and again commence the entire cycle of generating all of the required system timing signals in a highly stable and precise manner.

Considering now only FIG. 5b, the contents of memory means 125 may be written from either keyboard data entry means 42 or from an external source via external data lines 43. The (BCD-coded) data lines 42a from the keyboard enter one data input port 160A of a two-input-port data multiplex means 160, which has external data lines 43 coupled to its remaining data input port 160B. External control line 41 is coupled to the input-port-select (SEL') input of multiplexer means 160 in such manner as to cause external data input port 160B to be coupled to the multiplex means output port 160c if the SEL' input is energized, as by means of a switch 161 in series with a positive potential, representing activation of the SEL' lines by some external device (not shown); deactivation of the SEL' input causes data keyboard means output lines 42a to be coupled to multiplex means output port 160c. The keyboard data entry means also provides a strobe output (KSTB) whenever a data key is depressed, as well as providing a D pulse on line 163, if the data (D) key is depressed, and a BP pulse on a line 164, if the breakpoint (BP) key is depressed. The external means, such as the aforementioned computer and the like, provide its own strobe (CSTB) when transmitting data and also provides an external breakpoint (EBP) input and an external data (ED) input, each being OR'd to the BP and D lines 164 and 163, respectively.

A plurality of data latch means 171-174 sequentially receive the binary-coded data from multiplexer means output port 160c. In our preferred embodiment, this data is in binary-coded-decimal form, whereby each data latch means receives a four-line input and generates a four-line output; as previously mentioned, a total of four decades of data are utilized for setting each time interval, whereby the number of data latch means is set equal to four, although it should be understood that more or less data latch means and other data coding means may be utilized with the number of output lines forming the data bus, to memory means 125, being dictated by the desired system parameters and the arrangement of the memory means.

The data for a breakpoint is entered or modified by initially transmitting the number of the desired breakpoints (0 to 7 in the preferred embodiment) to the data inputs of first data latch means 171, simultaneously with a data strobe pulse on common latch means strobe line 179, to store the BP number in first data latch means 171. The data strobe pulse arrives via an OR gate 178 from either the keyboard strobe KSTB line or an external strobe CSTB line. The BCD-coded breakpoint number loaded into first data latch means 171 appears at the output thereof, and is coupled via a set of breakpoint address lines 180 to the data inputs of write address latch means 177. The BP key of keyboard means 42 is depressed to generate a pulse on the BP line 164 (or the EBP line is pulsed) to generate a strobe (BP=STB) to the write address latch means strobe input 177a. The desired breakpoint number is loaded into write address latch means 177 and appears at the write-input port 122a of the address multiplex means 122. Generation of a pulse on BP line 164 causes the SEL input of multiplexer means 122 to receive (by known means not shown for purposes of simplicity and indicated by broken line connection 183) the proper signal to couple write-input port 122a through the multiplexer means to memory means address input port 125a, furnishing the memory means with the address of the breakpoint about to have its data modified.

The four decades of the desired new breakpoint data are entered by depressing the data D key to enable and latch the D line 163, coupled as one input to a two-input AND gate 185. Alternatively, the ED line may be energized and held by the external computers and the like. Each of the four decimal numbers is entered by depressing the appropriate number key (or by energizing lines 43), preferably by entry commencing with the most significant digit and ending with the least significant digit. The first digit appears as BCD-coded data as the inputs to first data latch means 171, coincident with the appearance of a KSTB or a CSTB strobe on data-strobe line 179, causing loading of the first digit into the first data latch means. The strobe on line 179 appears at the remaining input of the AND gate 185 to energize the clock C input of a count-to-4 means 187. A first (0') output 187a of means 187 is coupled to an externally available READY line and is utilized, when energized, to indicate to an external programming device that zero digits of the data have been sent to the memory writing circuitry of the system synchronizer and that the circuitry is now ready to receive this data. The first count pulse arriving at means 187 removes the 0' count at output 187a and simultaneously energizing a $\overline{4'}$ output 187b to indicate to the external programming device that some, but less than all, data has been received and that the flaw detection system is now in a BUSY state.

Receipt of the second digit of data at the inputs of first data latch means 171 is also accompanied by a pulse on common strobe line 179, whereby the first digit data previously loaded into first data latch means 171 and now available at the output thereof is loaded into second data latch means 172, while the new data (second digit) available at the inputs of first data latch means 171 is now loaded therein. The new pulse on common strobe line 179 appears at count input C of means 187 to advance the output counter to 2 whereby the 0' output remains de-energized, while the $\overline{4'}$ line remains energized, and a third (4') output 187c is also de-energized as the count is less than four. Similarly, the third and fourth digit data patterns are received at the input of first data latch means 171 simultaneous with a pulse on common strobe line 179, to cause the first digit data to be sequentially stored in third latch means 173 and, finally, in fourth data latch means 174, while the second digit data moves from the first data latch means to the second data latch means, and finally, is stored in third data latch means 171. The third and fourth digits data will be finally stored in the second and first data latch means 172 and 171, respectively, after receipt of the fourth pulse on common strobe line 175. The third common strobe pulse arrives at the count C input to count means 187 and advances the output state thereof to decimal 3, whereby the 0' (READY) and 4' outputs remain de-energized and the $\overline{4'}$ (BUSY) line remains energized. Upon receipt of the fourth pulse from common strobe line 179, the output of counter-to-four means 187 reaches a data pattern equal to decimal 4; both the 0' output 187a and the $\overline{4'}$ output 187b are now de-energized and the third (4') output 187c is energized. The 4' output is coupled to the read-write control input 125b of the memory means, and upon being energized, causes the data stored in data latch means 171–174 (and now available upon the data bus to the input) to be stored at the address previously programmed for the memory means. Thus, the four decades of data for the selected breakpoint are modified.

In the event of incorrect data entry of one or more digits, a data-clear (DCLR) switch means 188 may be closed to couple a logic one to a first input of a two-input AND gate 189 having its other input coupled via a logic inverter means 190 to the BP line 164. If the BP line is low (signifying that a breakpoint strobe is not presently occurring) the output 189 of the AND gate is energizable by DCLR switch 188 to provide a suitable level on a common reset line 192 to data latch means 171–174 to reset the outputs of each thereof to zero and allow the correct data to be entered. The leading edges of the DCLR or BP or D signals may each be detected by known means to provide a reset pulse, at a reset input 187d of the count-to-four means, whereby means 187 is reset to a zero-count output to facilitate entry of new data.

Figure 6:
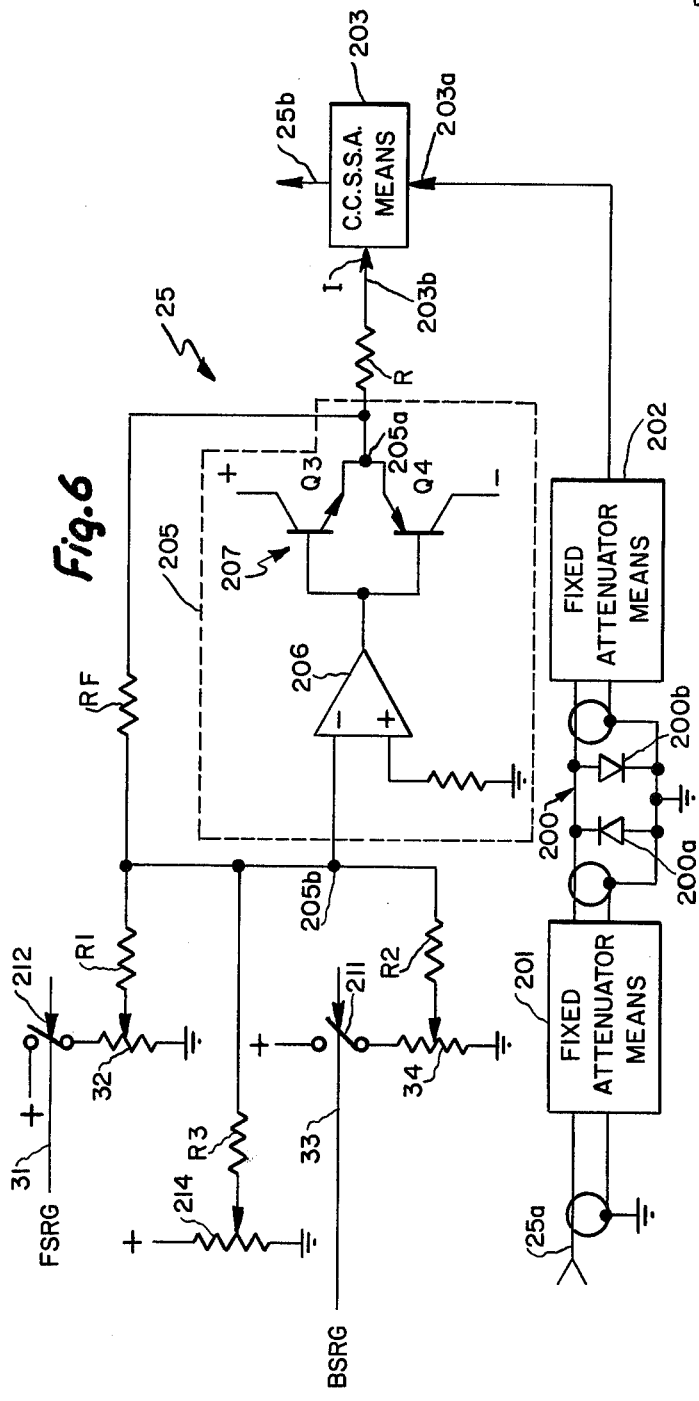
FIG. 6 is a schematic block diagram of one embodiment of surface encounter attenuator means.

Referring now to FIG. 6, surface encounter attenuator means 25 comprises a voltage limiter means 200, including a pair of opposed polarity diodes 200a and 200b, inserted between a pair of fixed attenuator means 201 and 202, between the SEA means input 25a and the input 203a of a current controlled solid state attenutator (CCSSA) means 203. Voltage limiter 200 serves to prevent unusually large reflection amplitudes from reaching either the CCSSA means or the subsequent circuitry coupled to the output 25b thereof, to facilitate establishing relatively constant operating conditions for the following circuitry. Fixed attenuator means 201 and 202 serve to isolate the variable impedance of the nonlinear devices 200a and 200b from both SEA means input 25a and the CCSSA means input 203a, to assure that the substantially constant input impedance $Z_{in}$ required of the SEA means is obtained, as well as to provide a substantially constant driving impedance for the CCSSA means. The increased, variable attenuation during FSRG and BSRG is provided by decreasing the current I flowing into a control input 203b of the CCSSA means. The attenuation of means 203 is greatest with a minimum magnitude of controlling current I and is least with a relatively large flow of current I. The attenuation-controlling current flows through a current source resistance R from the output of a high-output-current operational amplifier means 205 comprised of an integrated circuit operational amplifier 206 and a complementary-transistor current booster stage 207 using complementary transistors Q3 and Q4. A feedback resistor $R_F$ is coupled between the amplifier output 205a and the amplifier inverting (−) input 205b; each of a pair of input resistors $R_1$ and $R_2$ are connected between amplifier input 205b and one of the variable arms of either the FSRG attenuation-setting potentiometer 32 or the BSRG attenuation-setting potentiometer 34, respectively. One end of each of potentiometers 32 and 34 is coupled to a positive potential via respective normally-open switch means 210 and 211, respectively being closed responsive to the FSRG and BSRG signals. A third input resistance $R_3$ is coupled from amplifier input 205b to the variable arm of a normal-gain-setting potentiometer 214, always present in the circuit.

In operation, prior to receipt of either the FSRG or BSRG signals on one of lines 31 and 33, respectively, both switch means 210 and 211 are open, whereby the voltage at the amplifier output 205a is established responsive substantially solely to the position of the adjustable arm of the normal-gain-setting potentiometer 214. The normal-gain voltage at amplifier output 205a causes a normally high magnitude of current I to flow into input 203b of the CCSSA means, setting the relatively low normal attenuation thereof. Upon receipt of either of the FSRG or BSRG signals, the respective switch means 210 or 211 associated therewith is activated to couple an additional positive voltage to one of input resistors $R_1$ or $R_2$, respectively. The additional positive input voltage reduces the output voltage of inverting amplifier 205, whereby less current I flows through current-setting resistance R to the CCSSA means control input 203b, causing the attenuation of means 203 to increase in magnitude dependent upon the setting of potentiometers 32 or 34, for a time duration established by the duration of the signals on lines 31 and 33, respectively. Upon de-energization of both the FSRG and BSRG lines, the attenuation of the SEA means 25 reverts to the normal attenuation established by the setting of normal gain potentiometer 214, as required during the normal signal processing interval SPG.

Figure 7:
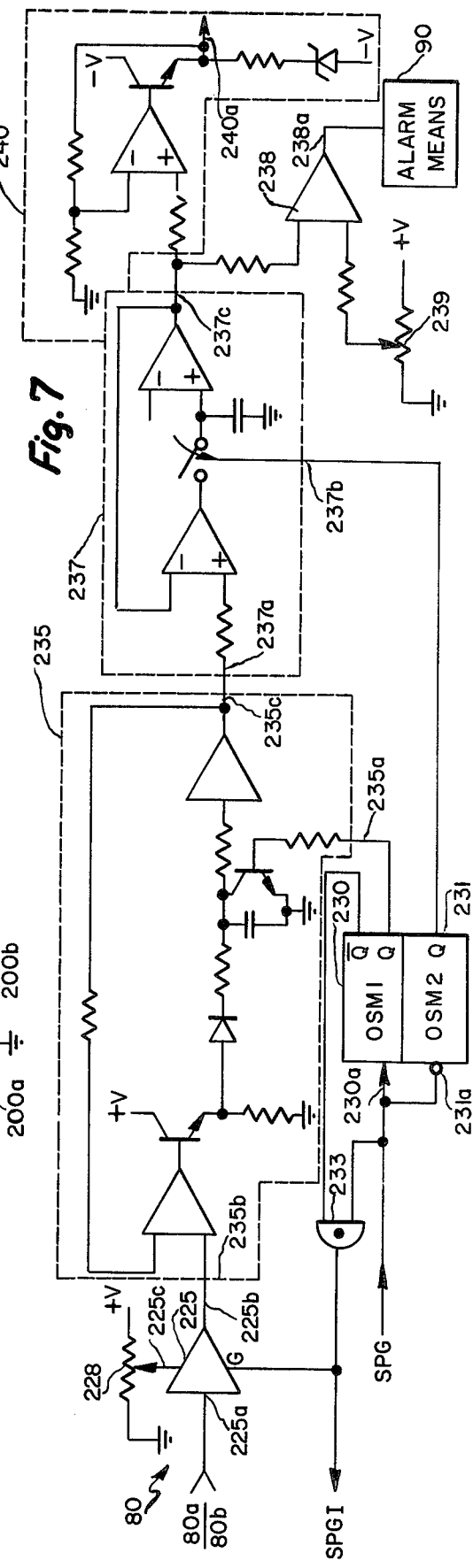
FIG. 7 is a schematic diagram of a portion of one embodiment of signal processor means.
Figure 8A:
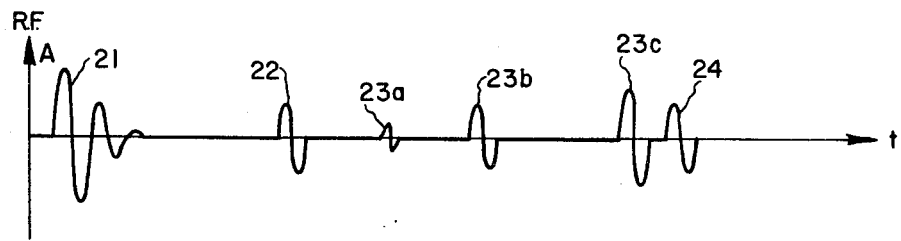
FIGS. 8a-8e are a set of graphs illustrating several of the steps in processing a system signal in the processor means of FIG. 7.
Figure 8B:
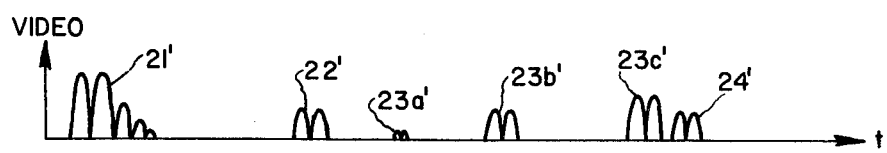
Figure 8C:
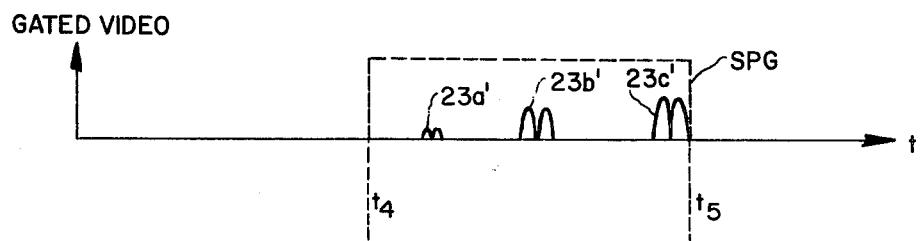
Figure 8D:
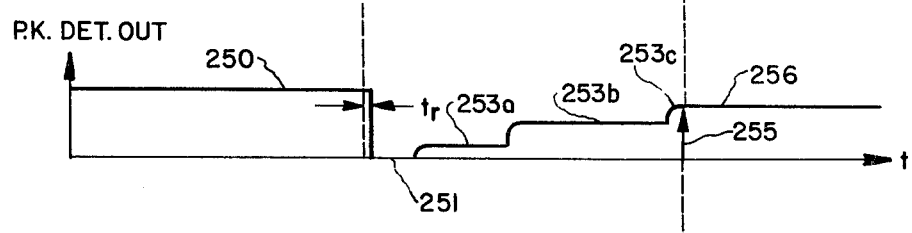
Figure 8E:
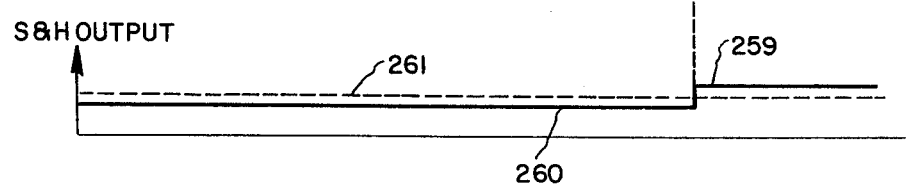

Referring now to FIGS. 7 and 8, one preferred embodiment of a signal processing means 80 comprises a gated amplifier 225, having a signal input 225a selectively coupled to one of signal processing means R.F. input 80a or full-wave rectified video input 80b. A gate input G may be enabled to reduce the magnitude of the signal at the gated amplifier output 225b substantially to zero, while the voltage established at a variable gain input 225c, by means of a gain-set potentiometer 228, is utilized to adjust the gain when the signal at gate input G enables output 225b.

The SPG signal is coupled to the positive-edge-triggered input 230a of a first one-shot multivibrator (OSM) means 230, to the negative-edge-triggering input 213a of a second one-shot multivibrator (OSM) means 231, and to one input of a two-input NAND gate 233, having its remaining input coupled to the $\overline{Q}$ output of OSM 230. The Q output of OSM 230 is coupled to the reset input 235a of a peak detector means 235 receiving the gated video signal at its signal input 235b and having an output 235c at which the greatest magnitude of all signals appearing at input 235b, between reset signals at input 235a, appears. Although one preferred form of resettable peak detector 235 is illustrated, it should be understood that many other forms of resettable peak detectors capable of forming an output indicative of the largest peak magnitude received during an interval between reset pulses, can be utilized. Peak detector output 235c is coupled to the input 237a of a sample and hold means 237, having a sample input 237b to control the time and duration of its sample mode of operation, and an output 237c at which the magnitude of the sampled input appears It should also be understood that, while one preferred form of sample-and-hold means 237 is partially schematically illustrated, many other sample-and-hold means are known and are generally equally as well utilized in our energy reflection flaw detection system. The output 237c of the sample-and-hold means is coupled to a threshold comparator 238, having its threshold level established by the setting of an adjustable arm of a threshold potentiometer 239, for actuating the comparator output 238a and, hence, an alarm means 90 coupled thereto. Additional gain and/or level-shifting stages, such as means 240 may be utilized to generate other outputs, such as output 240a, for detection and/or processing as required by the individual system.

In operation, one of R.F. signal input 80a (FIG. 8a) or full-wave rectified video input signal 80b (FIG. 8b) is coupled to gated amplifier 225. Prior to the commencement of the SPG signal, one input of AND gate 233 is at a binary-zero level, whereby the output thereof, generating the SPGI signal, is also at a binary-zero level; the video amplifier 225 is gated off, whereby a substantially zero signal appears at the peak detector input 235b. Upon arrival of the leading edge of the SPG waveform, first OSM means 230 is triggered, whereby its Q output is enabled to reset the peak detector, via its reset input 235a, and the $\overline{Q}$ output falls to a binary-zero level, disabling AND gate 233 (even though the SPG-derived input thereto is now at a binary-one level) until the first OSM means times out, after a time interval $T_r$. When OSM means 230 times out, both inputs to AND gate 230 are at the binary-one level, whereby the output of the gate is activated to the binary-one level, commencing generation of the SPGI signal for the duration of the SPG signal, and gating the video amplifier 225 to operate during the remaining duration of the SPG (as shown in the FIG. 8c, where the full-wave rectifier video input has been selected for amplification and gating by amplifier 225). Thus, the signal (FIG. 8d) at the output 235c of the peak detector means has some value 250 prior to the commencement of SPG at time $t_4$. During the short time interval $T_r$, thereafter, the peak detector output is reset and the level 251 immediately after reset is essentially zero. The appearance of the (full-wave rectified) reflection signal 23a', derived from first reflection signal 23a (see FIGS. 2 and 8a) causes the peak detector output to rise to the highest magnitude 253a thereof, which magnitude is held until a subsequent signal 23b' (responsive to reflection of energy from, e.g. the second flaw) having a large peak amplitude is received. The peak detector output is raised to the new, higher level 253b and maintained until any subsequent signal having a greater magnitude (such as peak amplitude 253c of the reflection signal 23c' from the third flaw) is received. Thus, at the time $t_5$ signifying the end of the SPG interval, the amplitude of the signal at peak rectifier output 235c is the amplitude of the largest flaw reflection signal received during the SPG interval.

Upon receiving the falling edge of the SPG signal, the negative-triggering input 235a of the second OSM means 231 generates a sampling pulse 255 at the Q output thereof, for causing sample-and-hold means 237 to acquire the maximum amplitude 256 from the peak detector. Simultaneously, the SPG signal is removed from gate 233 to cause the cessation of the SPGI signal and the signal at the gate input of video amplifier 225, reducing its output amplitude substantially to zero. The new voltage 259 now appearing at the sample-and-hold means output 237c is generally different from the level 260 thereat immediately prior to sample signal 255. If the new voltage 259 exceeds the threshold voltage 261 (shown in broken line in FIG. 8e) as established by threshold potentiometer 239, alarm means 90 is activated to signal detection of a flaw exceeding the preselected limits. Determination of the magnitude, position and other characteristics of the flaw may now be accomplished using the visual presentation on display means 83 (FIG. 1) or may be anaylzed by means of a computer and the like, receiving processed signal information from the auxiliary output 240a.

While one preferred embodiment of our novel energy reflection flaw detection system has been described herein, many variations and modifications will now become apparent to those skilled in the art. It is, therefore, our intent to be limited not by the present disclosure herein, but only by the scope of the appending claims.

What is claimed is:

1. An energy reflection flaw detection system for analyzing an object, comprising:
    means for generating a pulsed beam of energy toward and through said object;
    means for converting energy reflected from front and back surfaces of and flaws within said object into an electrical signal;
    system synchronization means having high stability and resolution for generating a plurality of system timing signals each independently variable with respect to the time at which the energy pulse is generated;
    first means enabled by at least one of the timing signals generated by said system synchronizer means for controllably highly attenuating at least one portion of said signal due to energy reflected by at least one of the back and front surfaces of said object, said first means transmitting another portion of said signal occurring between said front and back surface reflection signals with variable and relatively low attenuation;
    second means coupled to said first means for amplifying the attenuated signal;
    third means coupled to said second means for processing said signal responsive to a selected pair of said timing signals to determine the magnitude of at least one flaw within said object and received during a time interval between said pair of timing signals; and
    fourth means for performing an alarm function if the magnitude of the signal responsive to a flaw is greater than a predetermined set of flaw conditions.

2. A system as set forth in claim 1, further comprising fifth means coupled between said second and third means for full-wave rectifying said signal, whereby both polarity portions of a reflected signal are recovered and presented to said third means.

3. A system as set forth in claim 2, wherein said third means comprises:
    sixth means for amplifying a selectable one of the full-wave rectified signals from said fifth means and the non-rectified signals from said second means, only during said time interval
    seventh means for detecting the peak magnitude of an amplified signal from said sixth means; and
    eighth means for acquiring that one signal detected by said seventh means of greatest amplitude during said time interval.

4. A system as set forth in claim 1, further comprising manual means for establishing the time at which each signal from said system synchronizer means is generated;
    data port means for receiving information from means external to said system for establishing the time at which each signal from said system synchronizing means is generated; and
    means for selecting one of said manual means and said data port means for coupling to said system synchronizing means.

5. A system as set forth in claim 1, wherein said second means includes means for varying the gain thereof in accordance with the magnitude of a control signal.

6. A system as set forth in claim 5, further comprising means for establishing the control signal magnitude as a function of the time interval after generation of an energy pulse, to cause the output of said second means to compensate for the varying energy density of the beam when focussed at a point within said object.

7. A system as set forth in claim 6, wherein said control signal magnitude establishing means comprises:
    bistable means for providing first and second output voltages responsive respectively to generation of said energy pulse and the presence of another signal;
    means for integrating an input voltage to generate an output voltage having an amplitude changing with respect to time to provide said control signal;
    first and second potential sources of opposite polarities;
    first switch means for coupling said first potential source to the input of said integrating means responsive only to said first voltage being provided by said bistable means;
    second switch means for coupling said second potential source to the input of said integrating means responsive only to said second voltage being provided by said bistable means; and
    means for comparing the amplitude of said control signal against a reference voltage to generate said another signal if said control signal exceeds said reference signal.

8. A system as set forth in claim 1, wherein said first means further comprising means for attenuating said electrical signal with selectable magnitude in time-invariant manner between successive energy pulses.

9. A system as set forth in claim 1, wherein said first means comprises: means for variably attenuating said signal responsive to the magnitude of a second control signal;

means for providing a first magnitude of said second control signal to said attenuating means when a front surface reflection signal is expected to be present; and means for providing a second magnitude of said second control signal to said attenuating means when a back surface reflection signal is expected to be present.

10. A system as set forth in claim 9, wherein said first means further comprises means for establishing a maximum magnitude of said electrical signal for transmission to said attenuating means.

11. A system as set forth in claim 1, wherein said system synchronization means comprises master oscillator means for generating a highly stable periodic signal at a frequency equal to the reciprocal of a desired resolution interval;

means having a reset input and an output for counting the number of signals from said master oscillator means after a reset signal is received at said reset input and presenting data indicative of the count therein at said output;

memory means for storing a plurality of data words each representing one of a like plurality of timing intervals;

first comparator means receiving the output of said counting means and a first data word from said memory means associated with a total system time interval for generating said reset signal when the values of said data word and said counting means output are equal; and second comparator means receiving the output of said counting means and a sequential one of the data words for each consecutive remaining time interval after said total system time interval for generating an output upon the equivalence of each said data word and said counting means output to create at least said pair of timing signals and the signals to said frist means associated with said front and back surface reflection signals.

12. A system as set forth in claim 11, further comprising means coupled to said system synchronizing means for modifying the data stored within said memory means.

13. A system as set forth in claim 11, further comprising means for presenting the data associated with a next successive time interval to one of said first and second comparator means responsive to the generation of an output from one of said first and second comparator means.

14. A system as set forth in claim 1, further comprising means for visually displaying the amplitude of at least said electrical signal with respect to time elapsed after formation of each pulse beam of energy.

* * * * *